United States Patent
Ahmed et al.

US007754694B2

(10) Patent No.: US 7,754,694 B2
(45) Date of Patent: Jul. 13, 2010

(54) PYRROLO[2, 1-C][1, 4]BENZODIAZEPINE-GLYCOSIDE PRODRUG USEFUL AS A SELECTIVE ANTI TUMOR AGENT

(75) Inventors: Kamal Ahmed, Hydergabad (IN); Venkatesh Tekumalla, Hydergabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 12/015,023

(22) Filed: Jan. 16, 2008

(65) Prior Publication Data
US 2009/0036657 A1    Feb. 5, 2009

(30) Foreign Application Priority Data
Aug. 1, 2007    (IN)    ................ 1626/DEL/2007

(51) Int. Cl.
*A61K 31/70*    (2006.01)
*A61K 31/7028*    (2006.01)
*A61K 31/7042*    (2006.01)
*C07H 17/02*    (2006.01)

(52) U.S. Cl. .................. 514/25; 536/17.4; 536/4.1; 540/506

(58) Field of Classification Search ............... 536/17.4, 536/4.1; 514/23, 25; 540/506
See application file for complete search history.

(56) References Cited

OTHER PUBLICATIONS

Gura (Science, 1997, 278(5340):1041-1042).*

* cited by examiner

*Primary Examiner*—Shaojia Anna Jiang
*Assistant Examiner*—Michael C Henry
(74) *Attorney, Agent, or Firm*—Frank H. Foster; Kremblas & Foster

(57) ABSTRACT

The present invention provides pyrrolo[2,1-c][1,4]benzodiazepine-glycoside prodrug of general formula 1a-b, useful as selective anticancer agents. The present invention also provides a process for the preparation of pyrrolo[2,1-c][1,4] benzodiazepine-glycoside prodrugs of general formula 1a-b. This invention also provides activation of these prodrugs by *E.coli* β galactosidase and envisaged that these molecules are toxic to human cancer cell lines in the presence of the enzyme *E.coli* β-galactosidase. The prodrugs 1a and 1b were also found to be toxic to human cancer HepG2 cells even in the absence of the *E.coli* β-galactosidase. The toxic effect of the molecules when activated was similar to that of the parent molecules 6a and 6b, respectively.

15 Claims, 2 Drawing Sheets

Figure 1:
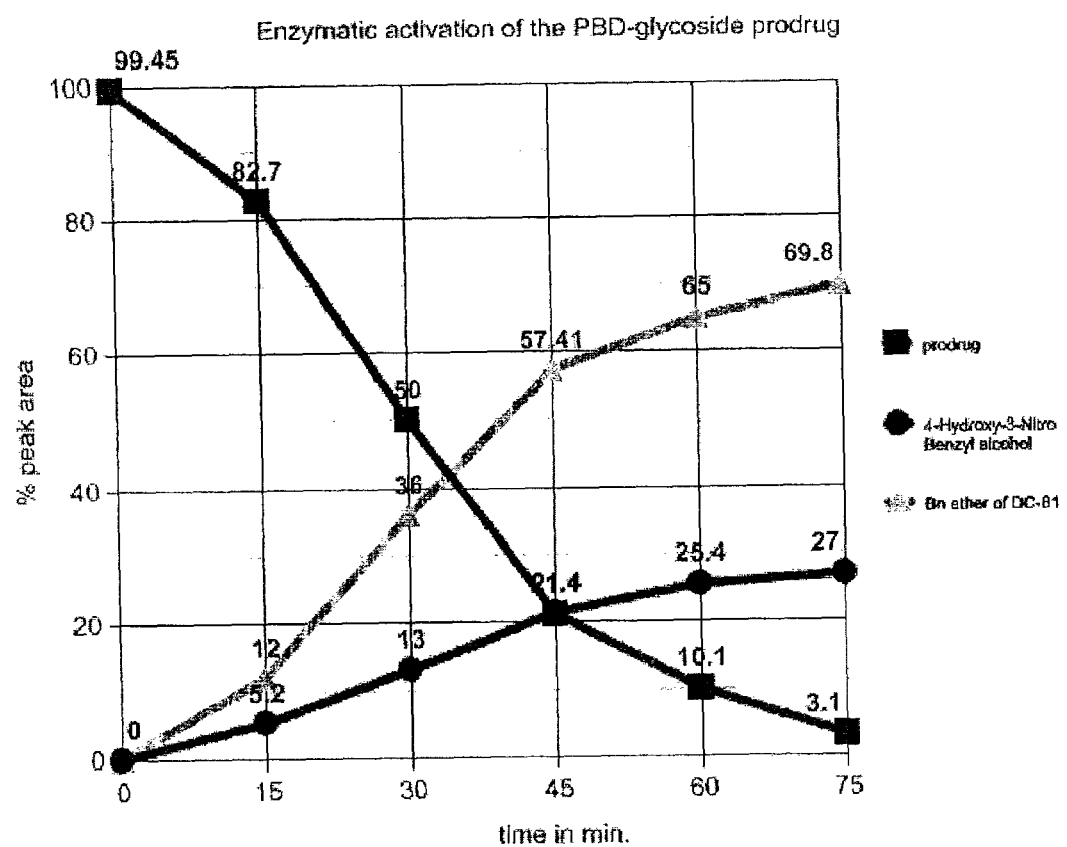

PYRROLO[2, 1-C][1, 4]BENZODIAZEPINE-GLYCOSIDE PRODRUG USEFUL AS A SELECTIVE ANTI TUMOR AGENT

CROSS-REFERENCES TO RELATED APPLICATIONS

This application claims foreign priority benefits under 35 U.S.C. 119(a)-(d) or (f) of application number 1626/DEL/2007 filed in India on Aug. 1, 2007 which is herein incorporated by reference.

STATEMENT REGARDING FEDERALLY-SPONSORED RESEARCH AND DEVELOPMENT (Not Applicable)

REFERENCE TO AN APPENDIX (Not Applicable)

FIELD OF THE INVENTION

The present invention relates to novel pyrrolo[2,1-c][1,4] benzodiazepine prodrug useful as a selective anti tumor agent for cancer therapy. Particularly, the present invention relates to (11S)-10-(4-ββ-D-galactopyranosyloxy-3-nitrophenyl)methoxy carbonyl-11-hydroxy-7-methoxy-1,2,3,-10,11,11a-hexahydro-5H-pyrrolo[2,1-c][1,4]-benzodiazepin-5-one] and 1,1'-[[(propane-1,3-diyl)dioxy]-bis(11S,11aS)-10-(4-β-D-galactopyranosyloxy-3-nitrophenyl)methoxycarbonyl-11-hydroxy-7-methoxy-1,2,3,-10,11,11a-hexahydro-5H-pyrrolo[2,1-c][1,4]-benzodiazepin-5-one]. The present invention also relates to a process for the preparation of novel pyrrolo[2,1-c][1,4] benzodiazepine (PBD-glycoside) prodrug useful as a selective anti tumor agent for cancer therapy. The present invention also relates to a process of activation of the PBD-glycoside prodrugs to drugs by the enzyme β-galactosidase.

The structural formula of novel PBD-gylcoside prodrugs is as follows,

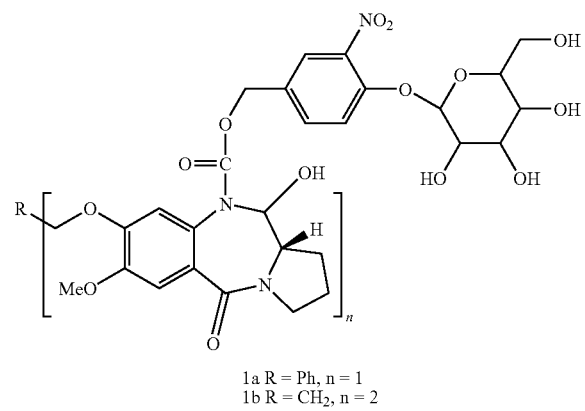

1a R = Ph, n = 1
1b R = CH$_2$, n = 2

BACKGROUND OF THE INVENTION

Prodrugs are modified form of drugs, which on activation form drugs. Recently some prodrugs of PBDs have been reported which do not get activated by the enzyme β-galactosidase (Marina J. Sagnou, Philip W. Howard, Stephen J. Gregson, Ebun Eno-Amooquaye, Philip J. Burke, David E. Thurston, *Bioorg Med Chem. Lett.* 2000, 10, 2083-2086; Jane M. Berry, Philip W. Howard, Lloyd R. Kelland, David E. Thurston, *Bioorg Med Chem. Lett.* 2002, 12, 1413-1416; Luke A. Masterson, Victoria J. Spanswick, John A. Hartley, Richard H. Begent, Philip W. Howard, David E. Thurston, *Bioorg. Med. Chem. Lett.* 2006, 16, 252-256).

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepines (PBDs). These PBDs are a family of sequence selective DNA-binding antitumour antibiotics that bind exclusively to the exocyclic N2-guanine in the minor groove of DNA via an acid-labile animal bond to the electrophilic imine at the N10-C11 position. (Kunimoto, S.; Masuda, T.; Kanbayashi, N.; Hamada, M.; Naganawa, H.; Miyamoto, M.; Takeuchi, T.; Unezawa, H. *J. Antibiot.,* 1980, 33, 665.; Kohn, K. W.; Speous, C. L. *J. Mol. Biol.,* 1970, 51, 551.; Hurley, L. H. Gairpla, C.; Zmijewski, M. *Biochem. Biophys. Acta.,* 1977, 475, 521.; Kaplan, D. J.; Hurley, L. H. *Biochemistry,* 1981, 20, 7572.; Ahmed Kamal, G. Ramesh, N. Laxman, P. Ramulu, O. Srinivas, K. Neelima, Anand K. Kondapi, V. B. Sreenu, H. A. Nagarajaram. *J. Med. Chem.* 2002, 45, 4679-4688).

All biologically active PBDs possess the (S) configuration at the chiral C11a position, which provides the molecule with a right-handed twist, which allows them to follow the curvature of the minor groove of B-form double-stranded DNA spanning three base pairs. The PBDs are of considerable current interest due to their ability to recognize and subsequently form covalent bonds to specific base sequences of double-stranded DNA. Naturally occurring pyrrolo[2,1-c][1, 4]benzodiazepines belong to a group of antitumour antibiotics derived from *Streptomyces* species with family members including anthramycin, tomaymycin, sibiromycin, chicamycin, neothramycins A and B, and DC-81.

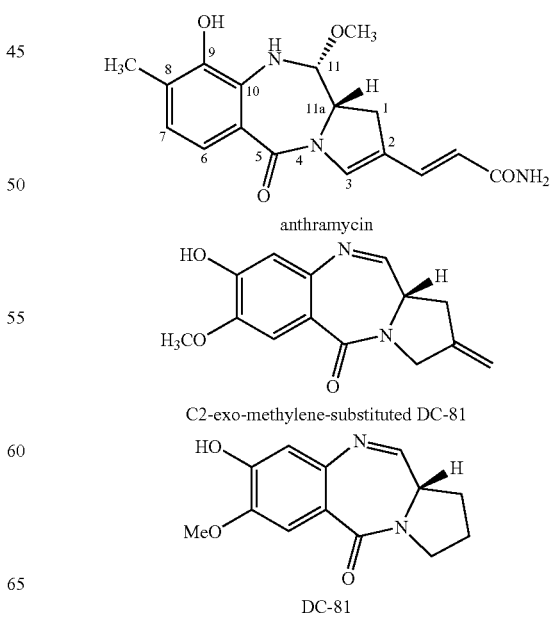

anthramycin

C2-exo-methylene-substituted DC-81

DC-81

-continued

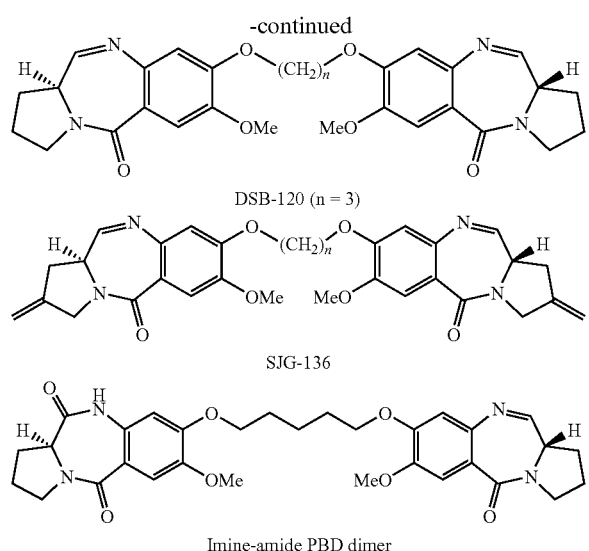

DSB-120 (n = 3)

SJG-136

Imine-amide PBD dimer

However, the clinical efficacy for these antibiotics is hindered by several limitations, such as poor water solubility and cardiotoxicity and development of drug resistance, lack of tumour selectivity, metabolic inactivation. Therefore it is of considerable interest to design and prepare glycoside prodrugs of PBDs that could be activated by the enzyme β-galactosidase. This enzyme is found in some tissues like liver specifically or it can be delivered as an enzyme-antibody conjugate to the malignant cells. It is expected that these prodrugs get activated by the enzyme to the active moiety, and then interact with DNA.

OBJECTIVES OF THE INVENTION

The main objective of the present invention is to provide novel pyrrolo[2,1-c][1,4]benzodiazepine prodrug with increased water solubility useful as selective antitumour agent.

Another objective of the present invention is to provide novel pyrrolo[2,1-c][1,4]benzodiazepine prodrug, which could be activated to drugs in the presence of the enzyme β-galactosidase.

Yet another object of the present invention is to provide a process for the preparation of novel pyrrolo[2,1-c][1,4]benzodiazepine-glycoside prodrug useful as antitumour agent for selective therapy of cancer.

SUMMARY OF THE INVENTION

Accordingly the present invention provides novel pyrrolo[2,1-c][1,4]benzodiazepine-glycoside prodrug of formula 1 useful as a selective anti tumour agent.

Formula 1

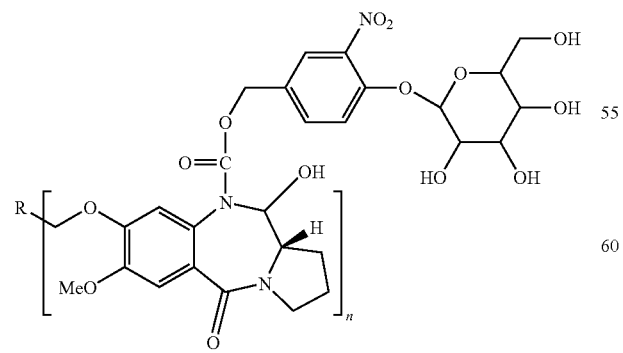

1a R = Ph, n = 1
1b R = CH$_2$, n = 2 wherein R=Phenyl or CH$_2$ and n=1 or 2.

In an embodiment of the present invention the representative compounds of formula 1 are as follows:

(11S)-10-(4-β-D-galactopyranosyloxy-3-nitrophenyl) methoxy carbonyl-11-hydroxy-7-methoxy-1,2,3,-10,11,11a-hexahydro-5H-pyrrolo[2,1-c][1,4]-benzodiazepin-5-one] (1a) and 1,1'-[[(propane-1,3-diyl)dioxy]-bis(11S,11aS)-10-(4-β-D-galactopyranosyloxy-3-nitrophenyl)methoxycarbonyl-11-hydroxy-7-methoxy-1,2,3,-10,11,11a-hexahydro-5H-pyrrolo[2,1-c][1,4]-benzodiazepin-5-one] (1b).

In yet another embodiment the compound of formula 1 is useful as anti tumour agent for selective therapy of cancer.

In yet another embodiment compound of formula 1 is activated to drug by the enzyme E. coli β-galactosidase.

In yet another embodiment compound of formula 1 is toxic to human cancer cell line A375 in the presence of E. coli β-galactosidase.

In yet another embodiment compound of formula 1 is toxic to human cancer cell line HeG2 in the absence of E. coli β-galactosidase.

The present invention further provides a process for the preparation of pyrrolo [2,1-c][1,4] benzodiazepine-glycoside prodrug of formula 1 useful as a selective anti tumour agent,

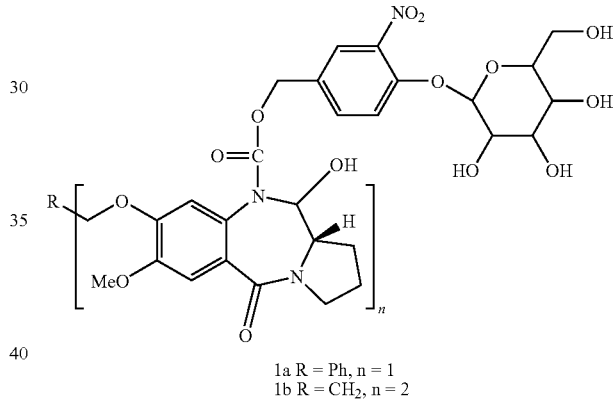

1a R = Ph, n = 1
1b R = CH$_2$, n = 2 wherein R=phenyl or CH$_2$ and n=1 or 2, and the said process comprising the steps of:

a. reacting the compound of formula 2$_{a-b}$ with triethylamine and triphosgene in dry dichloromethane, under stirring for a period of 20-30 minutes, evaporating the dichloromethane from the resultant mixture and redissolving it in tetrahydrofuran followed by filtration to remove the white solid mass, evaporation of the tetrahydrofuran from the resultant filtrate and redissolving the residue obtained in dichloromethane and reacting it with a compound of formula 5 in the presence of catalytic amount of dibutyl tin dilaurate, under stirring for a period of 6-7 hrs to obtain the desired compound of formula 3$_{a-b}$

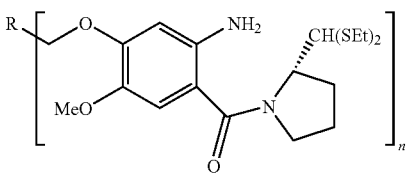

2a where R = Ph and n = 1
2b where R = —CH2— and n = 2

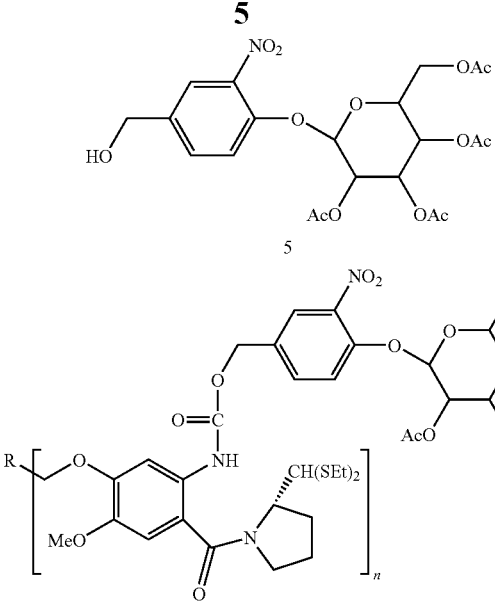

3a where R = Ph and n = 1
3b where R = —CH2— and n = 2 b. reacting the compound of formula $3_{a,b}$ obtained in step (a) with calcium carbonate and mercuric chloride in a solvent mixture of acetonitrile and water in a ratio of about 3:1, under stirring for a period of 10-14 hrs, followed by filtration and evaporation of acetonitrile from the filtrate and finally extraction with ethylacetate, drying and purification of the resultant extract by known method to obtain the desired compound of formula $4_{a,b}$

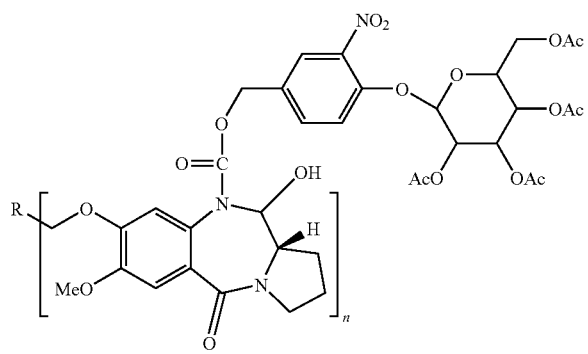

4a where R = Ph and n = 1
4b where R = —CH2— and n = 2 c. reacting the compound of formula $4_{a,b}$ obtained in step (b) with catalytic amount of NaOMe in methanol, at a temperature in the range of 0-5° C., for a period of 20-35 minutes to obtain the desired compound of formula $1_a$.

In an embodiment of the present invention the compound of formula 2 used in step (a) is selected from [(2-Amino-4-benzyloxy-5-methoxy-1,4-phenylene) carbonyl] (2S)-pyrrolidine-2-carboxaldehyde diethylthioacetal (2a) and 1,1β-[(Propane-1,3-diyl)dioxy]-bis[(2-amino-5-methoxy-1,4-phenylene)carbonyl]]-bis(2S)-pyrrolidine-2-carboxaldehyde diethylthioacetal (2b).

In yet another embodiment the compound of formula 5 used in step (a) is (4-β-D-2,3,4,6-tetra-O-acetylgalactopyranosyloxy-3-nitrophenyl) methanol.

In yet another embodiment the compound of formula 3 obtained in step (a) is selected from [2-amino-N-(4-β-D-2,3,4,6-tetra-O-acetylgalactopyranosyloxy-3-nitrophenyl)methoxycarbonyl-4-benzyloxy-5-methoxy-1,4-phenylene]carbonyl] (2S)-pyrrolidine-2-carboxaldehyde diethylthioacetal (3a) and 1,1β-[(Propane-1,3-diyl)oxy]-bis[(2-amino-N-(4-β-D-2,3,4,6-tetra-O-acetylgalactopyranosyloxy-3-nitrophenyl)methoxycarbonyl-5-methoxy-1,4-phenylene)carbonyl]]-bis[(2S)-pyrrolidine-2-carboxaldehyde diethylthioacetal (3b).

In yet another embodiment the compound of formula 4 obtained in step (b) is selected from (11S)-10-(4-β-D-2,3,4,6-tetra-O-acetylgalacto pyra nosyloxy-3-nitrophenyl)methoxycarbonyl-11-hydroxy-7-methoxy-1,2,3-10,11,11a-hexahydro-5H-pyrrolo[2,1-c][1,4]-benzodiazepin-5-one] (4a) and 1,1β-[(Propane-1,3-diyl)dioxy]-bis(11S,11aS)-10-(4-β-D-2,3,4,6-tetra-O-acetyl galactopyranosyloxy-3-nitrophenyl)methoxycarbonyl-11-hydroxy-7-methoxy-1,2,3,-10,11,11a-hexahydro-5H-pyrrolo[2,1-c][1,4]-benzodiazepin-5-one] (4b).

In yet another embodiment, the representative compounds of formula 1 obtained are (11S)-10-(4-β-D-galactopyranosyloxy-3-nitrophenyl) methoxy carbonyl -11-hydroxy-7-methoxy-1,2,3,-10,11,11a-hexahydro-5H-pyrrolo[2,1-c][1,4]-benzodiazepin-5-one] (1a) and 1,1'-[[(propane-1,3-diyl) dioxy]-bis(11S, 11aS)-10-(4-β-D-galactopyranosyloxy-3-nitrophenyl)methoxycarbonyl-11-hydroxy-7-methoxy-1,2,3,-10,11,11a-hexahydro-5H-pyrrolo[2,1-c][1,49-benzodiazepin-5-one] (1b).

BRIEF DESCRIPTION OF THE INVENTION

FIG. 1. A drawing illustrating the effect of the prodrug 1a 1 μmole was treated with 2 units of *E. coli* β galactosidase enzyme and the progress of the hydrolysis was monitored by reverse phase HPLC. HPLC conditions: C18 Reverse phase column. Mobile phase 40:60 $CH_3CN/H_2O$, flow rate of 1 ml/min. UV detection: wave length 254 nm.

Figure 2:
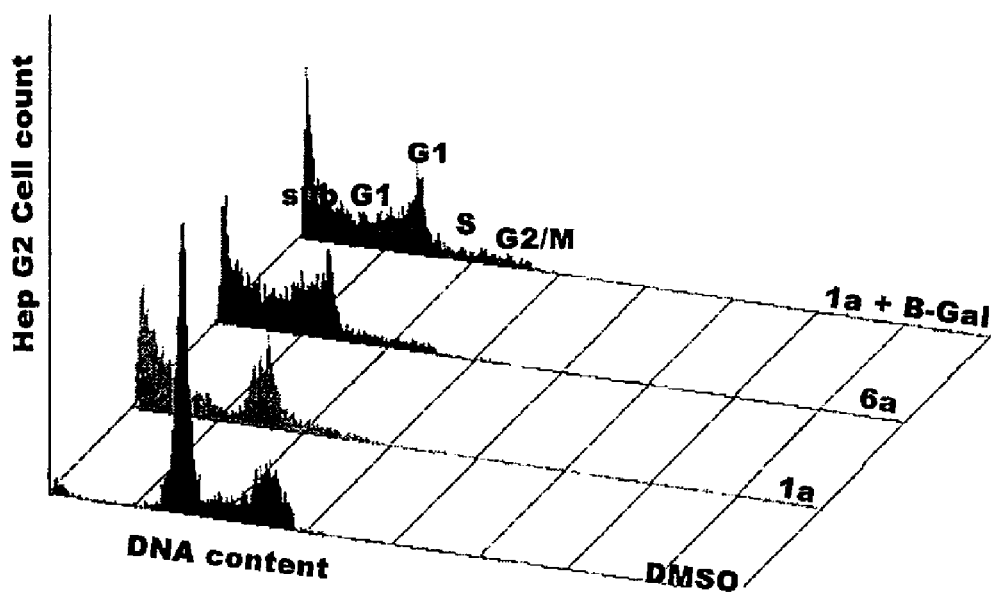

FIG. 2. A drawing illustrating a histogram overlay of HepG2 cells treated with compounds 1a, 6a and 1a+ *E.coli* β-galactosidase enzyme. It can be observed that the effect of the prodrug without any added enzyme is similar to that of the active molecule, benzylated ether of DC-81. The profile of the prodrug with *E.coli* enzyme added is also comparable to that of the DC-81.

DETAILED DESCRIPTION OF THE INVENTION

The present invention provides a process for the preparation of new pyrrolo[2,1-c][1,4]benzodiazepine-glycoside prodrugs, of formula 1a and 1b, useful as agents for selective therapy of solid tumours.

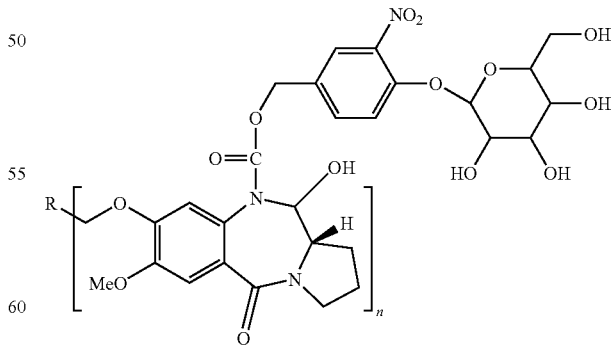

1a R = Ph, n = 1
1b R = $CH_2$, n = 2

The detail reaction scheme involved in the present invention is shown below:

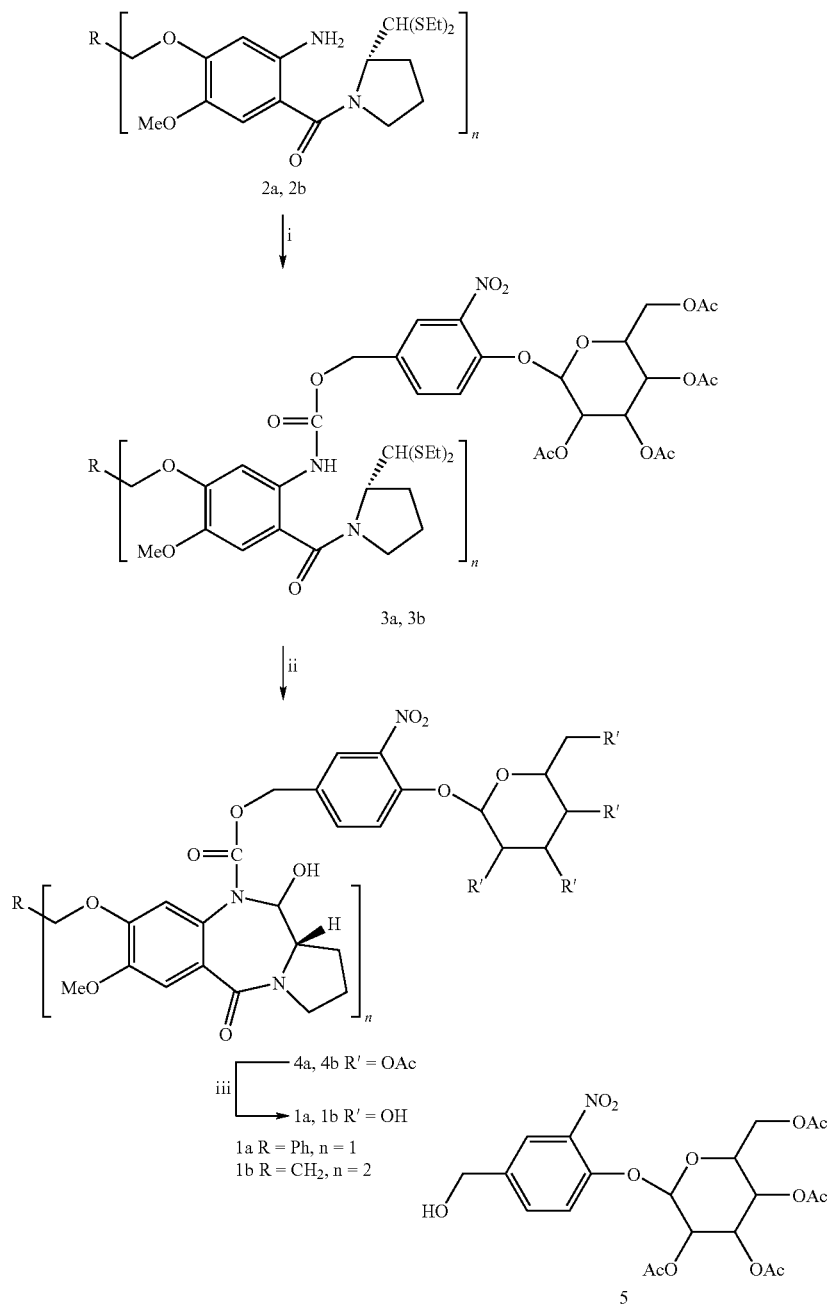

Reagents and conditions:
i a) triethyl amine, triphosgene, 25 min, b) compound 6, dibutyl tin dilaurate;
ii HgCl$_2$, CaCO$_3$, CH$_3$CN/H$_2$O, 4:1;
iii MeOH, catalytic amount NaOMe, 0-5° C., 30 min Reagents and conditions: i) a) triethyl amine, triphosgene, 25 min, b) compound 6, dibutyl tin dilaurate; ii) HgCl$_2$, CaCO$_3$, CH$_3$CN/H$_2$O, 4:1; iii) MeOH, catalytic amount NaOMe, 0-5° C., 30 min The following examples are given by way of illustration and therefore should not be construed to limit the scope of present invention.

EXAMPLE

Synthetic procedures for the preparation of the prodrugs 1a and 1b

Compound 2a and/or 2b (0.9 g, 1.95 m .mol 2a or 1.3 g, 1.66 mmol 2b) was taken in dry CH$_2$Cl$_2$, to which triethylamine (4.29 m .mol, 0.6 ml for 2a and 7.30 m. mol, 1.02 ml for 2b) and triphosgene (0.64 m.mol, 0.19 g for 2a and 1.09 mmol, 0.32 g for 2b) were added and stirred for 25 minutes, after which CH$_2$Cl$_2$ was evaporated and the reaction mixture was disolved in THF and was filtered leaving behind a white solid. The THF in the filtrate was evaporated and the residue was redissolved in CH$_2$Cl$_2$ and comp. 6 (1.95 m .mol, 0.97 g for 2a and 3.32.m mol, 1.65 g for 2b) and catalytic amount of dibutyl tin dilaurate were added and stirred for 6 hours to get the desired compound. The reaction mixture was washed with brine dried with anhydrous sodium sulfate and purified by column chromatography (1.53 g, 1.56 m mol, of 3a 80% yield and 2.46 g, 1.16 m mol, of 3b, 70% yield).

Compound 3a Yield=1.53 g, (80%); $^1$H NMR (CDCl$_3$, 300 MHz) δ 7.95 (bs, 1H), 7.84 (d,1H, J=2.26), 7.56 (dd, 1H, J=2.07, J$_2$=8.49), 7.49-7.45 (m, 2H), 7.41-7.31 (m, 4H), 6.92 (s, 1H), 5.55 (dd, 1H, J$_1$=7.93, J$_2$=10.57), 5.47 (dd, 1H, J$_1$=0.94, J$_2$=3.21), 5.18 (s, 2H), 5.15 (s, 2H), 5.10 (dd, 1H, J$_1$ =3.39, J$_2$ =10.57), 5.06 (d, 1H, J=7 .93), 4.68 (m, 2H), 4.28-4.04 (m, 3H), 3.83 (s, 3H), 3.61-3.54 (m, 2H), 2.80-2.59 (m, 4H), 2.33-1.86 (m, 16H), 1.97-1.36 (m, 6H), ESI-MS: m/z=1008 (M+Na)$^{30}$ Compound 3b Yield=2.46 g, (70%); $^1$H NMR,(CDCl$_3$, 400 MHz) δ 9.18 (bs, 1H, NH), 7.9-7.82 (m, 4H), 7.59-7.54 (m, 4H), 7.37 (s, 1H), 7.34 (s, 1H), 6.90 (s, 2H), 5.58-5.45 (m, 4H), 5.18-5.04 (m, 8H), 4.73-4.63 (m, 4H), 4.35-4.04 (m, 10H), 3.81 (s, 6H), 3.60-3.53 (m, 4H), 2.79-2.59 (m, 8H), 2.44-1.55 (m, 22H), 1.35-1.20 (m, 12H), ESI-MS: m/z=1853 (M+Na)$^+$ Compound 3a and/or 3b (1.4 g, 1.42 mmol 3a or 2g, 1.09 m. mol 3b) was taken in CH$_3$CN/H$_2$O 3:1 mixture, to it CaCO$_3$ (3.55 mmol, 0.35 g for 3a and 5.45 mmol, 0.54 g for 3b) and HgCl$_2$ (3.12 mmol, 0.84 g for 3a and 4.90 m.mol, 1.33 g for 3b) were added and stirred for 12 hrs. The reaction mixture was filtered through celite bed. Acetonitrile was evaporated from the filtrate and extracted with ethylacetate. The ethyl acetate extract was dried with anhydrous sodium sulfate. The solvent was evaporated and the compound was purified by column chromatography (yield 0.95 g, 1.09 mmol 76% of 4a and 1.31 g, 0.81 mmol, 75% of 4b).

Compound 4a Yield=1.09 g, (76%); $^1$H NMR (CDCl$_3$, 300 MHz) δ7.57 (s, 1H), 7.42-7.23 (m, 8H), 6.63 (s, 1H ), 5.59 (d, 1H, J=9.82), 5.52 (dd, 1H, J$_1$=7.55, J$_2$=10.57), 5.16-4.90 (m, 6H), 4.23-4.10 (m,3H), 3.93 (s, 3H), 3.75-3.43 (m, 3H), 2.20-1.55 (m, 16H), ESI-MS: m/z=902 (M+Na)$^+$ Compound 4b Yield=1.31 g, (75%); $^1$H NMR (CDCl$_3$, 500 MHz) δ 7.73-7.69 (m, 2H), 7.54-7.48 (m, 4H), 7.35-7.11 (m, 2H), 6.85 (s, 2H), 5.71 (d, 2H, J=9.82), 5.59 (dd, 2H, J$_1$=8.54, J$_2$=9.97), 5.46 (d, 2H, J=3.02), 5.30 (d, 2H, J$_1$=12.84), 5.07 (dd, 2H, J$_1$=3.02, J$_2$=10.57), 5.01 (d, 2H, J=7.55), 4.83 (d, 2H, J=12.08), 4.27-3.95 (m, 10H), 3.87 (s, 6H), 3.35-1.95 (m, 34H); ESI-MS m/z:1641 [M+Na]$^+$ Compound 4a and/or 4b (0.9 g, 1.02 mmol 4a or 1g, 0.61 mmol 4b) was dissolved in methanol and catalytic amount of NaOMe was added at 0° C. and stirred for 30 minutes to get the final compounds 1a and/or 1b. Compound 1a was purified by column chromatography to get 0.61 g, 0.86 mmol, 85% yield while the crude yield of 1b was 0.63 g, 0.49 mmol, 80%. Compound 1b was purified by preparative reverse phase HPLC.

Compound 1a Yield=0.61 g, (85%); $^1$H NMR (CD$_3$OD, 500 MHz) δ 7.60-7.53 (m, 1H), 7.45-7.24 (m, 7H), 7.21(s, 2H), 6.91-6.81(m, 1H), 5.66 (d, 1H; J=9.73), 5.13-4.92 (m, 5H), 3.89 (s, 3H), 3.84-3.39 (m, 9H), 2.17-1.97 (m, 4H); HRMS [M+Na]$^+$ calcd for C34H38N3O14 m/z=712.2353, found (FAB) m/z=712.2336

Compound 1b Yield=0.63 g, (80%); $^1$H NMR (CD3OD, 500 MHz) δ 7.72-7.32 (m, 6H), 7.21(s, 2H), 7.00-6.90 (m, 2H), 5.70 (d, 2H, J=8.97), 5.22 (d, 2H, J=11.73), 5.07-4.91 (m, 4H), 4.29-4.03 (m, 4H), 3.96-3.92 (in, 2H), 3.90-3.82 (m, 8H), 3.78-3.71 (s, 6H), 3.66-3.58 (m, 4H), 3.54-3.42 (in, 4H), 2.30-2.23 (m, 2H), 2.20-1.99 (m, 8H); ESI-MS: mz=1305 (M+Na)$^+$; HRMS [M+Na]$^+$ calcd for C57H66N6O28Na m/z=1305.3822, found (FAB) m/z=1305.3802.

Activation of the prodrugs by the enzyme β-galactosidase

The prodrugs of structural formula 1a and 1b were activated to their corresponding carbinolamines that are equivalent to their parent imines under the conditions mentioned below:
1. In the presence of the enzyme β-galactosidase.
2. Time duration of 60-90 minutes.
3. Temperature 37° C.
4. At a pH of 7.2 (phosphate buffer)

Mechanism of activation of the prodrug 1a to 6a

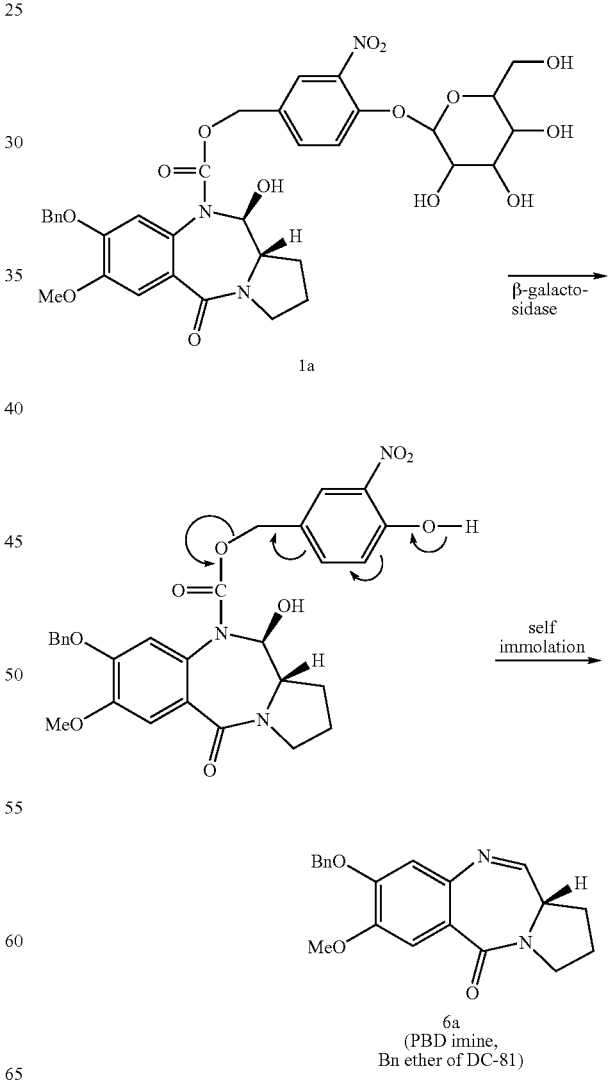

Mechanism of activation of the prodrug 1b to 6b

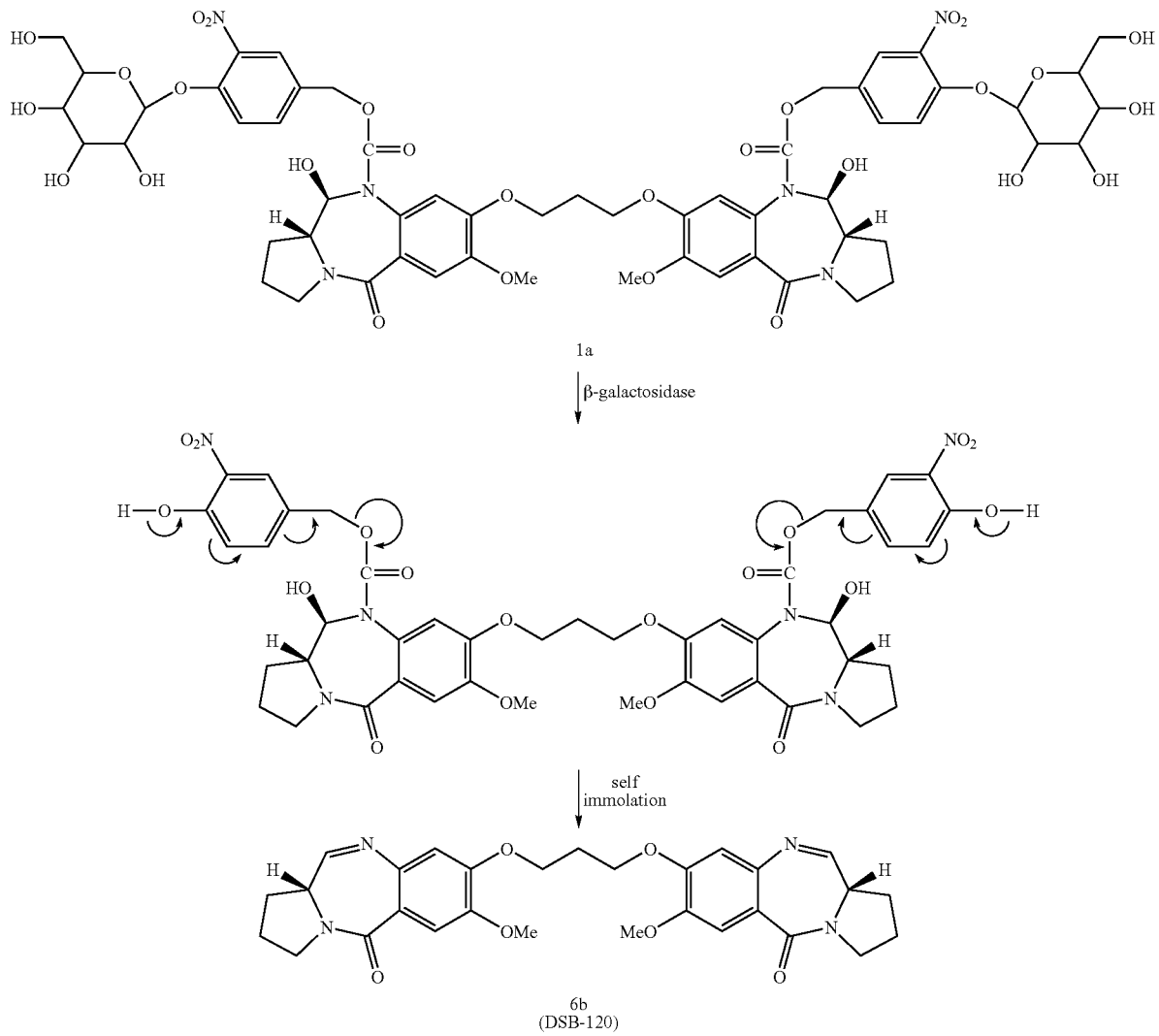

The prodrug 1a 1 μmole was treated with 2 units of *E. coli* β galactosidase enzyme and the progress of the hydrolysis was monitored by reverse phase HPLC. The results are presented in the form of a graph as illustrated in FIG. 1.

Biological Studies Of The Prodrugs

The cytotoxic effects of the newly synthesized compounds 1a and 1b and their respective PBD imines were examined by cell cycle progression experiments on human tumor cells, by using fluorescence-activated cell sorting (FACS) analysis, in the absence and in the presence of β-galactosidase enzyme. In the primary flow cytometric study, the DNA content of the cells was used as a major determinant for cell count. The subG1 population, a conspicuous indicator for cell death, presumably apoptosis, and G2/M population was also determined in HepG2 and A375 cell lines.

The cytometric assay of A375 cells treated with both the prodrugs 1a and 1b along with *E. coli* β-galactosidase, not only resulted in apoptosis identical to that of the parent drugs 6a and 6b respectively, but also the amount of cell death was insignificant in the absence of the enzyme, indicating the prodrugs to be nontoxic even at such a high concentration (1a 42 μM and 1b 23.4 μM).

Next we evaluated the prodrugs for their activation efficiency by intracellular β-galactosidase, in human liver cancer, HepG2 cells. The cytometric assay of HepG2 cells with the prodrug 1a in the presence and in the absence of *E. coli* β-galactosidase enzyme was found to show an apoptotic response comparable to that of the parent drug 6a. Prodrug 1b in HepG2 cell line in the presence of *E. coli* β-galactosidase showed a profile comparable to that of the parent drug 6b. The prodrug with out the enzyme produced a block in the G2/M phase of the cell cycle, a characteristic of cross-linking drugs.

Picture representing the histogram overlay of HepG2 cells treated with compounds 1a, 6a and 1a+*E.coli* β-galactosidase enzyme is shown in FIG. 2. It can be observed that the effect of the prodrug without any added enzyme is similar to that of the active molecule, benzylated ether of DC-81. The profile of the prodrug with *E.coli* enzyme added is also comparable to that of the DC-81.

The PBD glycoside prodrugs 1a and 1b are found to be useful for selective therapy of cancer especially solid tumours, with minimal toxic effect on the normal tissues.

The invention claimed is:

1. A pyrrolo [2,1-c][1,4]benzodiazepine-glycoside prodrug of formula 1

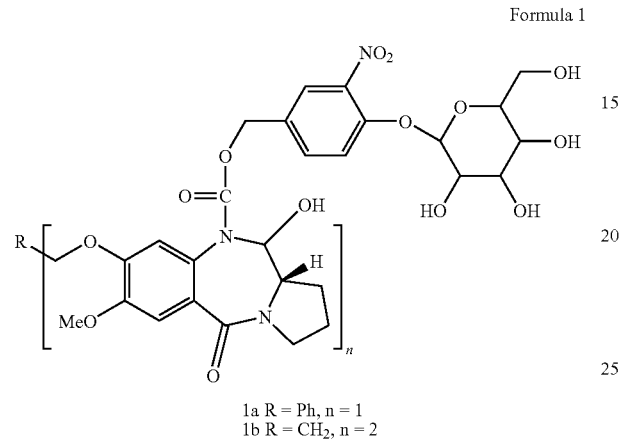

1a R = Ph, n = 1
1b R = CH₂, n = 2 wherein R=Ph or CH$_2$ and n=1 or 2.

2. The prodrug according to claim 1, wherein the prodrug of formula 1 is selected from a group consisting of (11S)-10-(4-β-D-galactopyranosyloxy-3-nitrophenyl) methoxy carbonyl-11-hydroxy-7-methoxy-1,2,3,-10,11,11a-hexahydro-5H-pyrrolo [2,1-c][1,4]-benzodiazepin-5-one] (a compound 1a), 1,1'-[[(propane-1,3-diyl)dioxy]-bis(11S,11aS)-10-(4-β-D-galactopyranosyloxy-3-nitrophenyl)methoxycarbonyl-11-hydroxy-7-methoxy-1,2,3,-10,11,11a-hexahydro-5H-pyrrolo[2,1-c][1,4]-benzodiazepin-5-one] (a compound 1b), and a mixture thereof.

3. The prodrug according to claim 1, wherein said prodrug of formula 1 is activated to a carbinolamine by the enzyme *E. coli* β-galactosidase.

4. A process for the preparation of pyrrolo [2,1-c][1,4] benzodiazepine-glycoside prodrug of formula 1

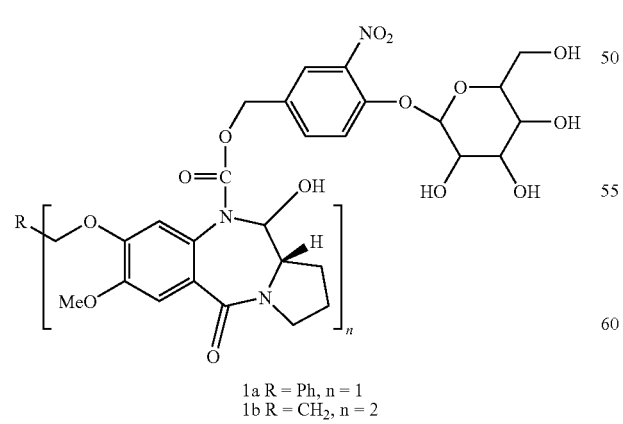

1a R = Ph, n = 1
1b R = CH₂, n = 2 wherein R=Ph or CH$_2$ and n=1 or 2, and the said process comprising the steps of:

a. reacting a compound 2, which is selected from a group consisting of a compound 2a, a compound 2b, and a mixture thereof, with triethylamine and triphosgene in dry dichloromethane, under stirring, for a period of 20-30 minutes, evaporating the dichloromethane from the resultant mixture and redissolving it in tetrahydrofuran followed by filtration to remove the white solid mass, evaporation of the tetrahydrofuran from the resultant filtrate and redissolving the residue obtained in dichloromethane and reacting it with a compound 5 in the presence of catalytic amount of dibutyl tin dilaurate, under stirring for a period of 6-7 hrs to obtain a compound 3, which is selected from a group consisting of a compound 3a, a compound 3b, and a mixture thereof;

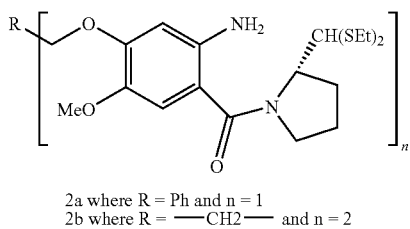

2a where R = Ph and n = 1
2b where R = —CH2— and n = 2

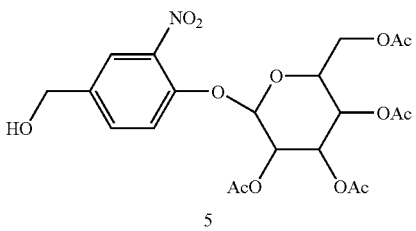

5

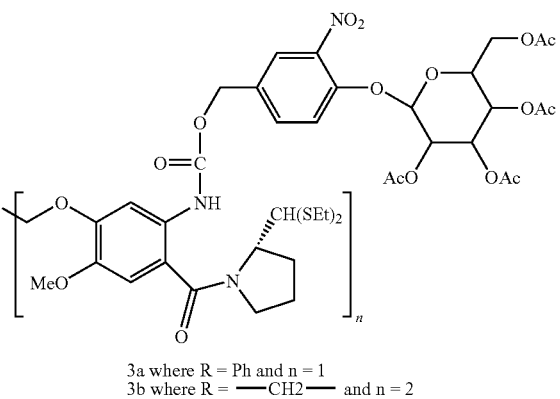

3a where R = Ph and n = 1
3b where R = —CH2— and n = 2 b. reacting the compound 3 obtained in step (a) with calcium carbonate and mercuric chloride in a solvent mixture of acetonitrile and water in a ratio of about 3:1, under stirring for a period of 10-14 hrs, followed by filtration and evaporation of acetonitrile from the filtrate and finally extraction with ethylacetate, drying and purification of the resultant extract by known method to obtain a compound 4, which is selected from a group consisting of a compound 4a, a compound 4b, and a mixture thereof

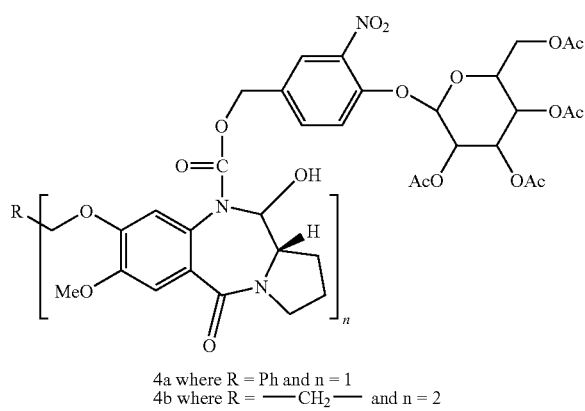

4a where R = Ph and n = 1
4b where R = —CH$_2$— and n = 2 c. reacting the compound 4 obtained in step (b) with catalytic amount of NaOMe in methanol, at a temperature in the range of 0-5° C., for a period of 20-35 minutes to obtain the prodrug of formula 1.

5. The process according to claim 4, wherein the compound 2 used in step (a) is selected from a group consisting of [(2-Amino-4-benzyloxy-5-methoxy-1,4-phenylene) carbonyl] (2S)-pyrrolidine-2-carboxaldehyde diethylthioacetal (the compound 2a) and 1,1β-[[(Propane-1,3-diyl)dioxy]-bis[(2-amino-5-methoxy-1,4-phenylene)carbonyl]]-bis[(2S)-pyrrolidine-2-carboxaldehyde diethylthioacetal (the compound 2b).

6. The process according to claim 4, wherein the compound 5 used in step (a) is (4-β-D-2,3,4,6-tetra-O-acetylgalactopyranosyloxy-3-nitrophenyl) methanol.

7. The process according to claim 4, wherein the compound 3 obtained in step (a) is selected from a group consisting of [2-amino-N-(4-β-D-2,3,4,6-tetra-O-acetylgalacto pyranosyloxy-3-nitrophenyl)methoxycarbonyl-4-benzyloxy-5-methoxy-1,4-phenylene]carbonyl] (2S)-pyrrolidine-2-carboxaldehyde diethylthioacetal (the compound 3a) and 1,1β-[(Propane-1,3-diyl)ioxy]-bis[(2-amino-N-(4-β-D-2,3,4,6-tetra-O-acetylgalactopyranosyloxy-3-nitrophenyl) methoxycarbonyl-5-methoxy-1,4-phenylene)carbonyl]]bis (2S)-pyrrolidine-2-carboxaldehyde diethylthioacetal (the compound 3b).

8. The process according to claim 4, wherein the compound 4 obtained in step (b) is selected from a group consisting of (11S)-10-(4-β-D-2,3,4,6-tetra-O-acetylgalacto pyra nosyloxy-3-nitrophenyl)methoxycarbonyl-11-hydroxy-7-methoxy-1,2,3,-10,11,[11a-]hexahydro-5H-pyrrolo[2,1-c][1,4]-benzodiazepin-5-one] (the compound 4a) and 1,1β-[(Propane-1,3-diyl)dioxy]-bis(11S,11aS)-10-4-β-D-2,3,4,6-tetra-O-acetyl galactopyranosyloxy-3-nitrophenyl) methoxycarbonyl-11-hydroxy-7-methoxy-1,2,3,-10,11,11a-hexahydro-5H-pyrrolo [2,1-c] [1,4]-benzodiazepin-5-one] (the compound 4b).

9. The process according to claim 4, wherein the prodrug of formula 1 obtained are selected from a group consisting of (11S)-10-(4-β-D-galactopyranosyloxy-3-nitrophenyl) methoxy carbonyl-11-hydroxy-7-methoxy-1,2,3,-10,11,11a-hexahydro-5H-pyrrolo [2,1-c][1,4]-benzodiazepin-5-one] (the compound 1a), 1,1'- [[(propane-1,3-diyl)dioxy]-bis (11S,11aS)-10-(4-β-D-galactopyranosyloxy-3-nitrophenyl) methoxycarbonyl-11-hydroxy-7-methoxy-1,2,3,-10,11,11a-hexahydro-5H-pyrrolo[2,1-c][1,4]-benzodiazepin-5-one] (the compound 1b), and a mixture thereof.

10. The process according to claim 4, further comprising a step of activating the prodrug of formula 1 to a carbinolamine compound by the enzyme *E. coli* β-galactosidase.

11. A method of inhibiting or reducing solid tumor cells sensitive to the prodrug of claim 1, comprising administering an effective amount of said prodrug to the said solid tumor cells, wherein said prodrug binds to DNAs of the tumor cells to inhibit the synthesis of the DNAs.

12. The method of claim 11, wherein the prodrug is activated to a carbinolamine compound by the enzyme *E. coli* β-galactosidase.

13. The method of claim 12, wherein the carbinolamine compound is pyrrolo [2,1-c][1,4]benzodiazepine.

14. The method of claim 11, wherein an effective amount of said prodrug is administered to a human cancer cell line A375 in the presence of *E. coli* (β-galactosidase.

15. A method of inhibiting or reducing solid tumour cells sensitive to the prodrug of claim 1, comprising administering an effective amount of said prodrug to a human cancer cell line HepG2 in the absence of *E. coli* β-galactosidase.

* * * * *